United States Patent [19]
Lal et al.

[11] Patent Number: 5,932,443
[45] Date of Patent: Aug. 3, 1999

[54] HUMAN ANTIGENS

[75] Inventors: Preeti Lal, Sunnyvale; Olga Bandman; Neil C. Corley, both of Mountain View; Purvi Shah, Sunnyvale, all of Calif.

[73] Assignee: Incyte Pharmaceuticals, Inc., Palo Alto, Calif.

[21] Appl. No.: 08/937,972

[22] Filed: Sep. 26, 1997

[51] Int. Cl.$^6$ .............................. C12N 15/12; C12N 1/21; C07H 21/04; A61K 48/00
[52] U.S. Cl. ........................... 435/69.1; 435/6; 435/91.2; 435/320.1; 435/252.3; 514/44; 536/23.5
[58] Field of Search ............................... 536/23.5; 435/6, 435/69.1, 91.2, 320.1, 257.3; 530/350; 424/185.1, 184.1; 514/12

[56] References Cited

PUBLICATIONS

Kroczek, RA. Southern and Northern analysis. J. Chromatog. 618:133–145, 1993.

Hiller, L., et al., GenBank Accession Number N32974, Jan. 10, 1996.

Rokeach, LA, et al., Mapping of the immunoreactive domains of a small nuclear ribonucleoprotein–associated Sm–D autoantigen. Clin. Immunol. Immunopath. 65(3):315–324, Dec. 1992.

Rokeach, L.A., et al., "Molecular cloning of a cDNA encoding the human Sm–D autoantigen", *Proc. Natl. Acad. Sci. USA*, 85: 4832–4836 (1988).

Mitsuda, T., et al., "The Murine Sm–D Autoantigen: Multiple Genes, Genetic Polymorphism, Evolutionary Conservation and Lack of Intervening Sequences in the Coding Region", *Journal of Autoimmunity*, 5: 277–287 (1992).

Szikora, J.P., et al., "Structure of the gene of tum transplantation antigen P35B: presence of a point mutation in the antigenic allele", *EMBO J.*, 9(4): 1041–1050 (1990).

Tonetti, M., et al., "Synthesis of GDP-$_L$-fucose by the Human FX Protein", *The Journal of Biological Chemistry*, 271(44): 27274–27279 (1996).

Springer, T.A., et al., "Sticky sugars for selectins", *Nature*, 349 (6306): 196–197 (1991).

Brandley, B.K., et al., "Carbohydrate Ligands of the LEC Cell Adhesion Molecules", *Cell*, 63(5): 861–863 (1990).

Feizi, T., et al., "Carbohydrates as antigenic determinants of glycoproteins", *Biochem J.*, 245(1): 1–11 (1987).

Rokeach, L.A., et al., (GI 338265) GenBank Sequence Database (Accession J03798), National Center for Biotechnology Information: National Library of Medicine, Bethesda, Maryland 20849, (Dec. 15, 1988).

Rokeach, L.A., et al., (GI 338264) GenBank Sequence Database (Accession J03798), National Center for Biotechnology Information: National Library of Medicine, Bethesda, Maryland 20849, (Dec. 15, 1988).

Szikora, J.P., et al., (GI 199586) GenBank Sequence Database (Accession M30127), National Center for Biotechnology Information: National Library of Medicine, Bethesda, Maryland 20849, (Dec. 16, 1992).

Szikora, J.P., et al., (GI 199585) GenBank Sequence Database (Accession M30127), National Center for Biotechnology Information: National Library of Medicine, Bethesda, Maryland 20849, (Dec. 16, 1992).

Tonetti, M., et al., (GI 1381179) GenBank Sequence Database (Accession U58766), National Center for Biotechnology Information: National Library of Medicine, Bethesda, Maryland 20849, (Oct. 31, 1996).

Tonetti, M., et al., (GI 1381178) GenBank Sequence Database (Accession U58766), National Center for Biotechnology Information: National Library of Medicine, Bethesda, Maryland 20849, (Nov. 1, 1996).

*Primary Examiner*—David Saunders
*Assistant Examiner*—Mary Beth Tung
*Attorney, Agent, or Firm*—Colette C. Muenzen; Lucy J. Billings; Incyte Pharmaceuticals, Inc.

[57] ABSTRACT

The invention provides two human antigens (ANTS) and polynucleotides which identify and encode ANTS. The invention also provides expression vectors, host cells, agonists, antibodies and antagonists. The invention also provides methods for treating disorders associated with expression of ANTS.

12 Claims, 11 Drawing Sheets

```
5' NCG CAC TCT GCG CCC GGA GGA CAG AGC GGC CCG GTC GCC ATG GTT TCT CCG
     9              18              27              36              45              54

TCC TGC TGC AGC CGG GAG GCA GCC AGT CCA GCC CGC CGC TAG CTT CGG CGG
     63              72              81              90              99             108

CGA CCC AGA CGG GGA AAG CGG GAA TGT CGC GTG CAA GCA GGC AGC TGG TGT
    117             126             135             144             153             162

GGA AGA ATG GCG GTG AGC CAT TCA GTG AAG GAG CGG ACC ATC TCT GAG AAC AGC
        171             180             189             198             207             216
         M   A   V   S   H   S   V   K   E   R   T   I   S   E   N   S

CTG ATC ATC CTA CTG CAG GGC CTC CAG GGC CGG GTA ACC ACT GTG GAC CTG CGG
        225             234             243             252             261             270
         L   I   I   L   L   Q   G   L   Q   G   R   V   T   T   V   D   L   R

GAT GAG AGC GTG GCC CAC CGC GGA CGC ATA GAC AAT GTC GAT GCT TTC ATG AAC ATC
        279             288             297             306             315             324
         D   E   S   V   A   H   R   G   R   I   D   N   V   D   A   F   M   N   I

CGC CTG GCC AAA GTC ACC TAC ACG GAC CGT TGG GGG CAT CAG GTC AAG CTG GAT
        333             342             351             360             369             378
         R   L   A   K   V   T   Y   T   D   R   W   G   H   Q   V   K   L   D
```

FIGURE 1A

```
     387         396         405         414         423         432
GAC CTC TTT GTG ACA GGC CGC AAT GTC CGC TAC CAC ATC CCA GAT GAC GTG
 D   L   F   V   T   G   R   N   V   R   Y   H   I   P   D   D   V 441         450         459         468         477         486
AAC ATC ACC TCG ACC ATT GAG CAG CTG CAG ATT ATC CAT CGG GTG CGA AAC
 N   I   T   S   T   I   E   Q   L   Q   I   I   H   R   V   R   N 495         504         513         522         531         540
TTT GGT GGC AAG GGC CAA GGC CGG TGG GAA TTT CCC CCA AAA AAC TGT AAG TGA
 F   G   G   K   G   Q   G   R   W   E   F   P   P   K   N   C   K 549         558         567         576         585         594
GGC CCT CAG CAA GCC CTG GCC CCA ACT CGG AGT CCT CCA GTG ATC TCC GGA GCT 603         612         621         630         639         648
AGT TCC CTG CCC TCA CAC CCT GTC TGG TAC CCG AGA AGA AAG CAG GGC CAG GCC 657         666         675         684         693         702
AGA AGC TGG TGT CCA ACA GAC ACC TGT CAA ACC TGT CTT TCA CAG GGT TCC 711         720         729         738         747         756
ACC TCC CAG ACT CAC TCT GGG ACC CAG AAT CCT ATA TGT GGC CTT GGG GTA GGT
```

FIGURE 1B

```
       765           774           783           792           801           810
GAC AAT CCC CCT TTT TGA TGA TCT GAA TCT CTG ACT TAT TGA TTA TGG AAC CTG 819           828           837           846           855           864
TCA AGT AGT TTT CAA CTC TCC CAG TGA GGA TAA TTA AAC ATG CTC AGC CTG AAA

873
AAA AAA AAA AAA A 3'
```

FIGURE 1C

```
  1  MAVSHSVKERTISENSLIILLQGLQGRVTTVDLRDESVAH  124208
  1  M---------------KLVRFLMKLSHETVTIELKNGTQVH  GI 338265

41  GRIDNVDAFMNIRLAKVTYTDRWGHQVKLDDLFVTGRNVR   124208
 27  GTITGVDVSMNTHLKAVKMTLKNREPVQLETLSIRGNNIR   GI 338265

81  YVHIPDDVNITS---TIEQQLQ-----IIHRVRNFG-GK    124208
 67  YFILPDSLPDTLLVDVEPKVKSKKREAVAGRGRGRGRGR    GI 338265

111  GQGRWEFPPKNCK                              124208
107  GRGRGRGGPRR                                GI 338265
```

FIGURE 2

```
                                 9            18           27           36           45           54
5' TGG NAG CCG GCG GTG GGG CTG GAC GCA GTG AGG TGG CAC CGG ACT CAG CCG CGC 63           72           81           90           99          108
   CCT GGG CCC TGG ATG TTC CGT GCA ACT GAC ATG GGT GAA CCC CAG GGA TCC ATG
                                                           M   G   E   P   Q   G   S   M 117          126          135          144          153          162
   CGG ATT CTA GTG ACA GGG GGC TCT GGG CTG GTA GGC AAA GCC ATC CAG AAG GTG
    R   I   L   V   T   G   G   S   G   L   V   G   K   A   I   Q   K   V 171          180          189          198          207          216
   GTA GCA GAT GGA GCT GGA CTT CCT GGA GAG GAC TGG GTG TTT GTC TCC TCT AAA
    V   A   D   G   A   G   L   P   G   E   D   W   V   F   V   S   S   K 225          234          243          252          261          270
   GAC GCC GAT CTC ACG GAT ACA GCA CAG ACC CGC GCC CTG TTT GAG AAG GTC CAA
    D   A   D   L   T   D   T   A   Q   T   R   A   L   F   E   K   V   Q 279          288          297          306          315          324
   CCC ACA CAC GTC ATC CAT CTT GCT GCA ATG GTG GGG GGC CTG TTC CGG AAT ATC
    P   T   H   V   I   H   L   A   A   M   V   G   G   L   F   R   N   I 333          342          351          360          369          378
   AAA TAC AAT TTG GAC TTC TGG AGG AAA AAC GTG CAC ATG AAC GAC AAC GTC CTG
    K   Y   N   L   D   F   W   R   K   N   V   H   M   N   D   N   V   L

FIGURE 3A
```

```
                387 396 405 414 423 432
CAC TCG GCC TTT GAG GTG GGC GCC AAG GTG TCC TGC CTG TCC ACC TGT
 H   S   A   F   E   V   G   A   K   V   S   C   L   S   T   C 441 450 459 468 477 486
ATC TTC CCT GAC AAG AGC ACG ACC TAC CCG ATA GAT GAG ACC ATG ATC CAC AAT GGG
 I   F   P   D   K   S   T   T   Y   P   I   D   E   T   M   I   H   N   G 495 504 513 522 531 540
CCT CCC AAC AGC CAC AAT TTT GGG TAC TCG TAT CCG TAT GCC AAG AGG ATG ATC GAC GTG
 P   P   N   S   H   N   F   G   Y   S   Y   P   Y   A   K   R   M   I   D   V 549 558 567 576 585 594
CAG AAC AGG GCC TAC TTC CAG CAG TAC GGC TGC ACC TTC ACC GCT GTC ATC CCC
 Q   N   R   A   Y   F   Q   Q   Y   G   C   T   F   T   A   V   I   P 603 612 621 630 639 648
ACC AAC GTC CTC ATC CAC GGG CCC CAC GAC AAC TTC AAC ATC GAG GAT GGC CAC GTG CTG
 T   N   V   L   I   H   G   P   H   D   N   F   N   I   E   D   G   H   V   L 657 666 675 684 693 702
CCT GGC CTC TTC GGG GCC TAC CTG GCC AAG GTG CAC TTC AGC AGC GGC TCG GCC CTG ACG
 P   G   L   F   G   A   Y   L   A   K   V   H   F   S   S   G   S   A   L   T 711 720 729 738 747 756
GTG TGG GGT ACA GGG AAT CCG CGG AGG CAG TTC ATA TAC TCG CTG GAC CTG GCC
 V   W   G   T   G   N   P   R   R   Q   F   I   Y   S   L   D   L   A
```

FIGURE 3B

```
      765         774         783         792         801         810
CAG CTC TTT ATC TGG GTC CTG CGG GAG TAC AAT GAA GTG GAG CCC ATC ATC CTC
 Q   L   F   I   W   V   L   R   E   Y   N   E   V   E   P   I   I   L 819         828         837         846         855         864
TCC GTG GGC GAG GAA GAT GAG GTC TCC ATC AAG GAG GCA GCC GAG GCG GTG GTG
 S   V   G   E   E   D   E   V   S   I   K   E   A   A   E   A   V   V 873         882         891         900         909         918
GAG GCC ATG GAC TTC CAT GGG GAA GTC ACC TTT GAT ACA ACC AAG TCG GAT GGG
 E   A   M   D   F   H   G   E   V   T   F   D   T   T   K   S   D   G 927         936         945         954         963         972
CAG TTT AAG AAA ACA GCC AGT AAC AGC AAG CTG AGG ACC TAC CTG CCC GAC TTC
 Q   F   K   K   T   A   S   N   S   K   L   R   T   Y   L   P   D   F 981         990         999        1008        1017        1026
CGG TTC ACA CCC TTC AAG CAG GCG GTG AAG GAG ACC TGT GCT TGG TTC ACT GAC
 R   F   T   P   F   K   Q   A   V   K   E   T   C   A   W   F   T   D 1035        1044        1053        1062        1071        1080
GAG TAC GAG CAG CGG AAG TGA AGC CGG AAG ACA GGA TCA GGT GCC AGC GGA
 E   Y   E   Q   R   K   *

1089        1098        1107        1116        1125        1134
AAC TAC GCT GGC AGA GCC CAG CGG CCA CCA CCC GTC AAC CCT GCC AGG AGC TGA
 N   Y   A   G   R   A   Q   R   P   P   P   V   N   P   A   R   S   *

CCA TCG GCT GGC AGA GCC CAG CGG CCA CCA CCC GTC AAC CCT GCC AGG AGC TGA
```

FIGURE 3C

```
         1143       1152       1161       1170       1179       1188
         GGG CAC CAC CCA GCA ACC TGG GCC TGC ATT CCA TCC GCT CTG CAG CCC CAA GCA 1197       1206       1215       1224       1233       1242
         TCT TTC CAG TGG GGC CCC CAT TCA CGT TGG TCC TCA GGG AAA CCA GGG TCC GGG 1251       1260       1269       1278       1287       1296
         GCA GGC CCG GCG CTT TGC TCC CCA CAG CCC CCT GCG CGT GTC CAC TCT GAT 1305       1314       1323       1332       1341       1350
         CCT GCA TCC CAC TCC CTG GGA GCC AAT AAA GTG CAT TTT CAC AGG CAA AAA AAA

```
1    MGEPQGSMRILVTGGSGLVGKAIQKVVADGAGLPGEDWVF    1318190
1    MGEPHGSMRILVTGGSGLVGRAIQKVVADGAGLPGEEWVF    GI 199586

41   VSSKDADLTDTAQTRALFEKVQPTHVIHLAAMVGGLFRNI    1318190
41   VSSKDADLTDAAQTQALFQKVQPTHVIHLAAMVGGLFRNI    GI 199586

81   KYNLDFWRKNVHMNDNVLHSAFEVGARKVVSCLSTCIFPD    1318190
81   KYNLDFWRKNVHINDNVLHSAFEVGARKVVSCLSTCIFPD    GI 199586

121  KTTYPIDETMIHNGPPHNSNFGYSYAKRMIDVQNRAYFQQ    1318190
121  KTTYPIDETMIHNGPPHSSNFGYSYAKRMIDVQNRAYFQQ    GI 199586

161  YGCTFTAVIPTNVFGPHDNFNIEDGHVLPGLIHKVHLAKS    1318190
161  HFCTFTAVIPTNVFGPYDNFNIEDGHVLPGLIHKVHLAKS    GI 199586

201  SGSALTVWGTGNPRRQFIYSLDLAQLFIWVLREYNEVEPI    1318190
201  SDSALTVWGTGKPRRQFIYSLDLARLFIWVLREYSEVEPI    GI 199586

241  ILSVGEEDEVSIKEAAEAVVEAMDFHGEVTFDTTKSDGQF    1318190
241  ILSVGEEDEVSIKEAAEAVVEAMDFNGGSHF             GI 199586

281  KKTASNSKLRTYLPDFRFTPFKQAVKETCAWFTDNYEQAR    1318190
271                                              GI 199586

321  K                                            1318190
271                                              GI 199586
```

FIGURE 4 ns
HUMAN ANTIGENS

FIELD OF THE INVENTION

This invention relates to nucleic acid and amino acid sequences of two new human antigens and to the use of these sequences in the diagnosis, prevention, and treatment of inflammation and disorders associated with cell proliferation and apoptosis.

BACKGROUND OF THE INVENTION

Human defense against inflammation and cancer employs a dual response system consisting of both cellular and humoral immune response. The cellular immune response utilizes lymphoid cells such as lymphocytes and accessory lymphoid cells, and the humoral immune response is provided by antibodies which recognize unique molecular determinants expressed in inflammation and cancer cells.

Autoimmune diseases are a class of inflammation-associated disorders characterized by immunogenic reaction against normal cellular constituents. Most autoimmune antigenicity is correlated with four small nuclear ribonucleoprotein polypeptides (snRNPs): snRNP B, B', D, and E. For example, antibodies specific for recognizing snRNPs are expressed ubiquitously in patients with lupus erythematosus. In particular, Sm-D is an snRNP autoantigen which is closely associated with rheumatic diseases. Sm-D is a 13.3 kDa protein which exhibits a potential immunoreactive determinant rich in Gly and Arg at its carboxy terminus (Rokeach, L. A. et al. (1988) Proc. Natl. Acad. Sci. 85: 4832–4836; Mitsuda, T. et al. (1992) J. Autoimmun. 5: 277–287).

Cancers or malignant tumors are characterized by continuous cell proliferation and cell death. Cancer cells have been shown to exhibit unique gene expression, and dozens of cancer-specific genetic markers, tumor antigens, have been identified. P35B, a tumor rejection antigen, was first identified in mouse. A point mutation in the P35B gene elicits a cytolytic T lymphocyte response but no detectable antibody response (Szikora, J. P. et al. (1990) EMBO J. 9:1041–1050). A human homolog of P35B, FX, is a homodimeric NADP(H)-binding protein of 68 kDa. FX acts as a combined epimerase and NADPH-dependent reductase in converting GDP-4-keto-6-D-deoxymannose to GDP-L-fucose (Tonetti, M. et al. (1996) J. Biol. Chem. 271: 27274–27279). GDP-L-fucose is the substrate of several facosyl-transferases involved in the biosysthesis of blood group ABH antigenic determinants. GDP-L-fucose is also utilized in synthesizing fucosylated glycoproteins and glycolipids which function in cell adhesion and recognition (Springer, T. A. and Lasky, L. A. (1991) Nature 329: 196–197; Brandley, B. K. et al. (1990) Cell 63: 861–863; and Feizi, T. and Childs, R. A. (1987) Biochem. J. 245: 1–11).

The discovery of two new human antigens and the polynucleotides encoding them satisfies a need in the art by providing new compositions which are usefull in the diagnosis, prevention and treatment of inflammation and disorders associated with cell proliferation and apoptosis.

SUMMARY OF THE INVENTION

The invention features two substantially purified polypeptides, designated individually as ANTS1 and ANTS2 and collectively as ANTS, having the amino acid sequences shown in SEQ ID NO:1 and SEQ ID NO:3.

The invention further provides an isolated and substantially purified polynucleotide sequence encoding the polypeptide ANTS1, comprising the amino acid sequence of SEQ ID NO:1 or fragments thereof and compositions comprising said polynucleotide sequence. The invention also provides a polynucleotide sequence which hybridizes under stringent conditions to the polynucleotide sequence encoding the amino acid sequence SEQ ID NO:1 or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2, or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1, or a fragment thereof, the method comprising the steps of: a) culturing the host cell containing an expression vector containing at least a fragment of the polynucleotide sequence encoding ANTS1 under conditions suitable for the expression of the polypeptide; and b) recovering the polypeptide from the host cell culture.

The invention also provides a pharmaceutical composition comprising a substantially purified ANTS1 having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising the amino acid sequence of SEQ ID NO:1.

Still further, the invention provides a purified agonist of the polypeptide of SEQ ID NO:1.

The invention also provides a method for stimulating cell proliferation comprising administering to a cell an effective amount of purified ANTS1.

The invention also provides a method for preventing or treating a disorder associated with an increase in apoptosis comprising administering to a subject in need of such treatment an effective amount of a pharmaceutical composition comprising purified ANTS1.

The invention also provides a method for preventing or treating cancer comprising administering to a subject in need of such treatment an effective amount of an antagonist of ANTS1.

The invention also provides a method for preventing or treating inflammation comprising administering to a subject in need of such treatment an effective amount of an antagonist of ANTS1.

The invention also provides a method for detecting a polynucleotide which encodes ANTS1 in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding ANTS1 in the biological sample. In one aspect the nucleic acid material of the biological sample is amplified by the polymerase chain reaction prior to hybridization.

Still further, the invention provides an isolated and substantially purified polynucleotide sequence encoding the polypeptide ANTS2, comprising the amino acid sequence of SEQ ID NO:3 or fragments thereof and compositions comprising said polynucleotide sequence. The invention also provides a polynucleotide sequence which hybridizes under stringent conditions to the polynucleotide sequence encoding the amino acid sequence SEQ ID NO:3 or fragments of said polynucleotide sequence. The invention further provides a polynucleotide sequence comprising the complement of the polynucleotide sequence encoding the amino acid sequence of SEQ ID NO:3, or fragments or variants of said polynucleotide sequence.

The invention also provides an isolated and purified sequence comprising SEQ ID NO:4, or variants thereof. In addition, the invention provides a polynucleotide sequence which hybridizes under stringent conditions to the polynucleotide sequence of SEQ ID NO:4. The invention also provides a polynucleotide sequence comprising the complement of SEQ ID NO:4, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:3, or a fragment thereof, the method comprising the steps of: a) culturing the host cell containing an expression vector containing at least a fragment of the polynucleotide sequence encoding ANTS2 under conditions suitable for the expression of the polypeptide; and b) recovering the polypeptide from the host cell culture.

The invention also provides a pharmaceutical composition comprising a substantially purified ANTS2 having the amino acid sequence of SEQ ID NO:3 in conjunction with a suitable pharmaceutical carrier.

The invention also provides a purified antagonist of the polypeptide of SEQ ID NO:3. In one aspect the invention provides a purified antibody which binds to a polypeptide comprising the amino acid sequence of SEQ ID NO:3.

Still further, the invention provides a purified agonist of the polypeptide of SEQ ID NO:3.

The invention also provides a method for stimulating cell proliferation comprising administering to a cell an effective amount of purified ANTS2.

The invention also provides a method for preventing or treating a disorder associated with an increase in apoptosis comprising administering to a subject in need of such treatment an effective amount of a pharmaceutical composition comprising purified ANTS2.

The invention also provides a method for preventing or treating cancer comprising administering to a subject in need of such treatment an effective amount of an antagonist of ANTS2.

The invention also provides a method for preventing or treating inflammation comprising administering to a subject in need of such treatment an effective amount of an antagonist of ANTS2.

The invention also provides a method for detecting a polynucleotide which encodes ANTS2 (SEQ ID NO:3) in a biological sample comprising the steps of: a) hybridizing the complement of the polynucleotide sequence which encodes SEQ ID NO:3 to nucleic acid material of a biological sample, thereby forming a hybridization complex; and b) detecting the hybridization complex, wherein the presence of the complex correlates with the presence of a polynucleotide encoding ANTS2 in the biological sample. In one aspect the nucleic acid material of the biological sample is amplified by the polymerase chain reaction prior to hybridization.

BRIEF DESCRIPTION OF THE FIGURES

FIGS. 1A, 1B, and 1C show the amino acid sequence (SEQ ID NO:1) and nucleic acid sequence (SEQ ID NO:2) of ANTS1. The alignment was produced using MACDNASIS PRO software (Hitachi Software Engineering Co. Ltd. San Bruno, Calif.).

FIG. 2 shows the amino acid sequence alignments between ANTS1 (124208; SEQ ID NO:1) and a human small nuclear ribonucleoprotein, Sm-D (GI 338265; SEQ ID NO:5), produced using the multisequence alignment program of DNASTAR software (DNASTAR Inc., Madison Wis.).

FIGS. 3A, 3B, 3C, and 3D show the amino acid sequence (SEQ ID NO:3) and nucleic acid sequence (SEQ ID NO:4) of ANTS2. The alignment was produced using MACDNASIS PRO software (Hitachi Software Engineering Co. Ltd. San Bruno, Calif.).

FIG. 4 shows the amino acid sequence alignments between ANTS2 (1318190; SEQ ID NO:3) and a mouse tumor rejection antigen, P35B (GI 199586; SEQ ID NO:6), produced using the multisequence alignment program of DNASTER software (DNASTAR Inc., Madison Wis.).

DESCRIPTION OF THE INVENTION

Figure 5A:
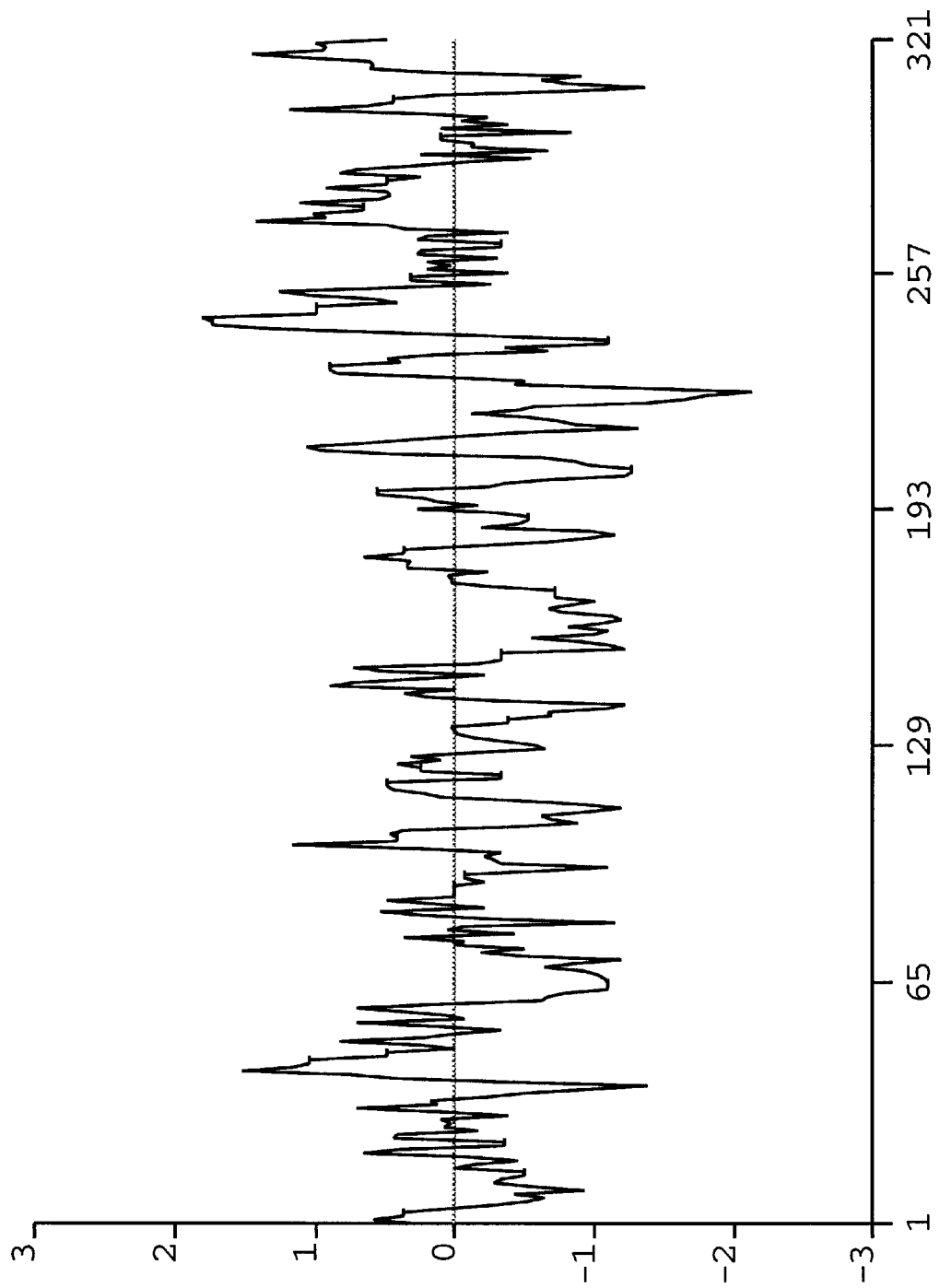
FIGS. 5A and 5B show the hydrophobicity plots for ANTS2 (SEQ ID NO:3) and P35B (SEQ ID NO:6), respectively. The positive X axis reflects amino acid position, and the negative Y axis, hydrophobicity (MACDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"ANTS", as used herein, refers to the amino acid sequences of substantially purified ANTS obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to ANTS, increases or prolongs the duration of the effect of ANTS. Agonists may include proteins, nucleic acids, carbohydrates, or any other molecules which bind to and modulate the effect of ANTS.

An "allele" or "allelic sequence", as used herein, is an alternative form of the gene encoding ANTS. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding ANTS as used herein include those with deletions, insertions, or substitutions of different nucleotides resulting in a polynucleotide that encodes the same or a functionally equivalent ANTS. Included within this definition are polymorphisms which may or may not be readily detectable using a particular oligonucleotide probe of the polynucleotide encoding ANTS, and improper or unexpected hybridization to alleles, with a locus other than the normal chromosomal locus for the polynucleotide sequence encoding ANTS. The encoded protein may also be "altered" and contain deletions, insertions, or substitutions of amino acid residues which produce a silent change and result in a functionally equivalent ANTS. Deliberate amino acid substitutions may be made on the basis of similarity in polarity, charge, solubility, hydrophobicity, hydrophilicity, and/or the amphipathic nature of the residues as long as the biological or immunological activity of ANTS is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of ANTS are preferably about 5 to about 15 amino acids in length and retain the biological activity or the immunological activity of ANTS. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to ANTS, decreases the amount or the duration of the effect of the biological or immunological activity of ANTS. Antagonists may include proteins, nucleic acids, carbohydrates, antibodies or any other molecules which decrease the effect of ANTS.

As used herein, the term "antibody" refers to intact molecules as well as fragments thereof, such as Fab, F(ab')$_2$, and Fv, which are capable of binding the epitopic determinant. Antibodies that bind ANTS polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic ANTS, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding ANTS (SEQ ID NO:1 or SEQ ID NO:3) or fragments thereof (e.g., SEQ ID NO:2, SEQ ID NO:4, and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR kit (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 or SEQ ID NO:4 by northern analysis is indicative of the presence of mRNA encoding ANTS in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to ANTS or the encoded ANTS. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of ANTS. For example, modulation may cause an increase or a decrease in protein activity, binding characteristics, or any other biological, functional or immunological properties of ANTS.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1 or SEQ ID NO:3" encompasses the full-length ANTS and fragments thereof.

The term "sample", as used herein, is used in its broadest sense. A biological sample suspected of containing nucleic acid encoding ANTS, or fragments thereof, or ANTS itself may comprise a bodily fluid, extract from a cell, chromosome, organelle, or membrane isolated from a cell, a cell, genomic DNA, RNA, or cDNA(in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions"or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of ANTS, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of two human antigens (hereinafter collectively referred to as "ANTS"), the polynucleotides encoding ANTS, and the use of these compositions for the diagnosis, prevention, or treatment of inflammation and disorders associated with cell proliferation and apoptosis.

Nucleic acids encoding the ANTS1 of the present invention were first identified in Incyte Clone 124208 from a lung tissue cDNA library (LUNGNOT01) using a computer search for amino acid sequence alignments. A consensus sequence, SEQ ID NO:2, was derived from the following overlapping and/or extended nucleic acid sequences: Incyte Clones 124208 (LUNGNOT01), 1708238 (PROSNOT16), and 1493210 (LUNGTUT03).

In one embodiment, the invention encompasses a polypeptide, ANTS1, comprising the amino acid sequence of SEQ ID NO:1, as shown in FIGS. 1A, 1B, and 1C. ANTS1 is 123 amino acids in length. ANTS1 has a potential immunoreactive determinant comprising a Gly-Arg(Lys)-rich motif close to its carboxy terminus, analogous to a human small nuclear ribonucleoprotein, Sm-D (GI 338265; SEQ ID NO:5). ANTS1 has one potential N-glycosylation site encompassing residues N89-S92; five potential casein kinase II phosphorylation sites encompassing residues S6-E9, T11–14, T29-D32, T58-D61, and S92-E95; and three potential protein kinase C phosphorylation sites encompassing residues S6-K8, T60-R62, and T75-R77. As shown in FIG. 2, ANTS1 has chemical and structural homology with Sm-D (GI 338265; SEQ ID NO:5). In particular, ANTS and Sm-D share 27% sequence homology. Northern analysis shows the expression of ANTS1 in various cDNA libraries, at least 45% of which are immortalized or cancerous, at least 15% of which involve immune response, and at least 23% are expressed in fetal/infant tissues or organs.

Nucleic acids encoding the ANTS2 of the present invention were first identified in Incyte Clone 1318190 from a bladder tissue cDNA library (BLADNOT04) using a computer search for amino acid sequence alignments. A consensus sequence, SEQ ID NO:4, was derived from the following overlapping and/or extended nucleic acid sequences: Incyte Clones 1318190 (BLADNOT04), 1693615 (COLNNOT23), 1852685 (LUNGFET03), 1350426 (LATRTUT02), and 547254 (BEPINOT01).

Figure 5B:
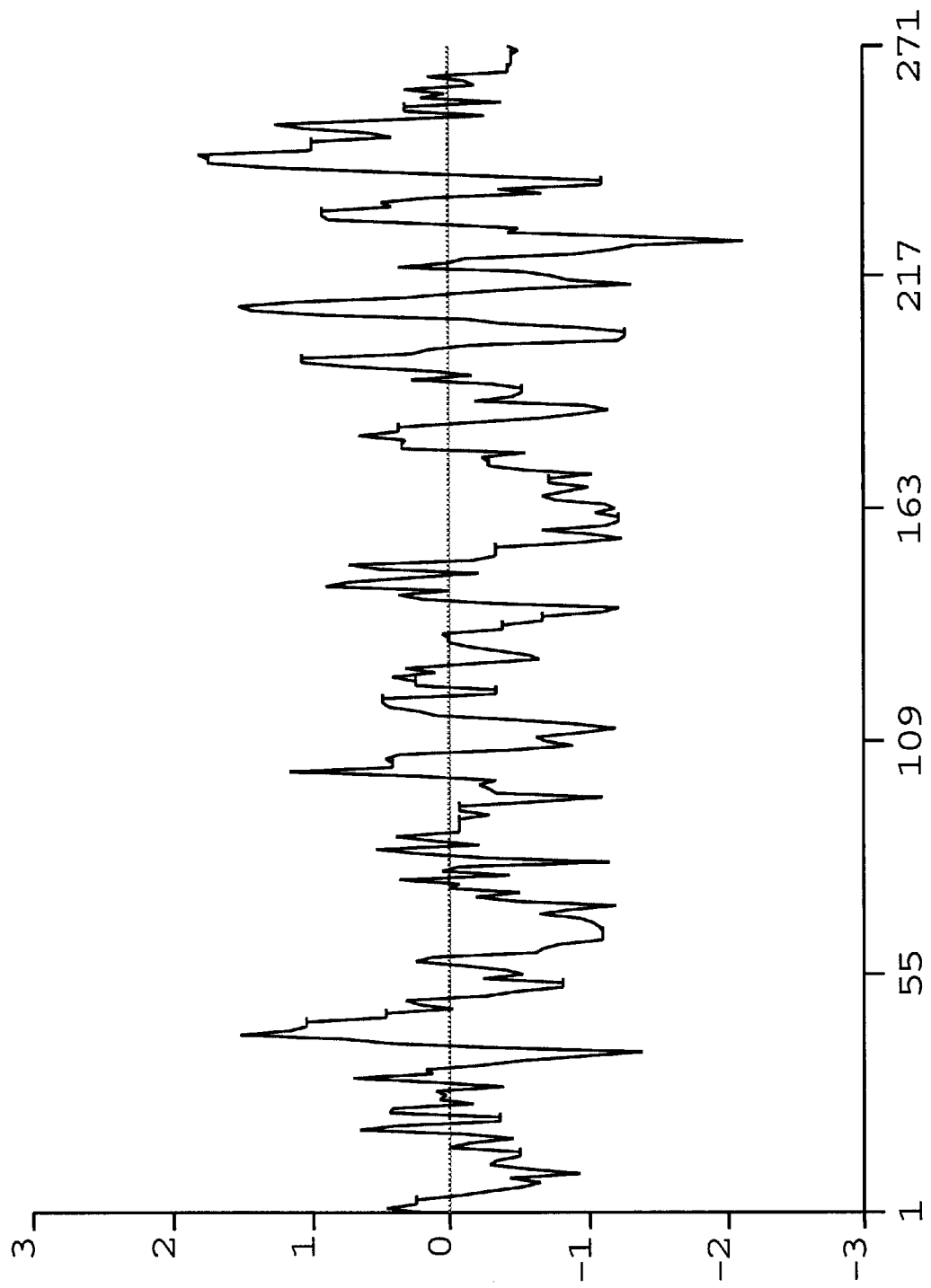

In another embodiment, the invention encompasses a polypeptide, ANTS2, comprising the amino acid sequence of SEQ ID NO:3, as shown in FIGS. 3A, 3B, 3C, and 3D. ANTS2 is 602 amino acids in length. ANTS2 has five potential casein kinase II phosphorylation sites encompassing residues S42-D45, S100-E103, S243-E246, S251-E254, and T274-D277; and four potential protein kinase C phosphorylation sites encompassing residues S7-R9, S42-K44, S251-K253, and T273-K275. As shown in FIG. 4, ANTS2 has chemical and structural homology with a mouse tumor rejection antigen, P35B (GI 199586; SEQ ID NO:6). In particular, ANTS2 and P35B share 94% sequence homology. As illustrated by FIGS. 5A and 5B, ANTS2 and P35B have rather similar hydrophobicity plots. Northern analysis shows the expression of ANTS2 in various cDNA libraries, at least 54% of which are immortalized or cancerous, at least 18% of which involve immune response, and at least 22% are expressed in fetal/infant tissues or organs.

The invention also encompasses ANTS variants. A preferred ANTS variant is one having at least 80%, and more preferably at least 90%, amino acid sequence identity to the ANTS amino acid sequence (SEQ ID NO:1 or SEQ ID NO:3) and which retains at least one biological, immunological or other functional characteristic or activity of ANTS. A most preferred ANTS variant is one having at least 95% amino acid sequence identity to SEQ ID NO:1 or SEQ ID NO:3.

The invention also encompasses polynucleotides which encode ANTS. Accordingly, any nucleic acid sequence which encodes the amino acid sequence of ANTS can be used to produce recombinant molecules which express ANTS. In a particular embodiment, the invention encompasses the polynucleotide comprising the nucleic acid sequence of SEQ ID NO:2, or SEQ ID NO:4 as shown in FIGS. 1A, 1B, and 1C, or FIGS. 2A, 2B, 2C and 2D.

It will be appreciated by those skilled in the art that as a result of the degeneracy of the genetic code, a multitude of nucleotide sequences encoding ANTS, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring ANTS, and all such variations are to be considered as being specifically disclosed.

Although nucleotide sequences which encode ANTS and its variants are preferably capable of hybridizing to the nucleotide sequence of the naturally occurring ANTS under appropriately selected conditions of stringency, it may be advantageous to produce nucleotide sequences encoding ANTS or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding ANTS and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode ANTS and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding ANTS or any fragment thereof.

Also encompassed by the invention are polynucleotide sequences that are capable of hybridizing to the claimed nucleotide sequences, and in particular, those shown in SEQ ID NO:2 or SEQ ID NO:4, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE DNA polymerase (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system (Life Technologies, Gaithersburg Md.). Preferably, the process is automated with machines such as the MICROLAB 2200 (Hamilton, Reno Nev.), Peltier thermal cycler 200 (PTC200; MJ Research, Watertown Mass.) and the ABI CATALYST and ABI PRISM 373 and 377 DNA sequence preparation and sequencing systems (Perkin Elmer).

The nucleic acid sequences encoding ANTS may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTER FINDER libraries (Clontech, Palo Alto, Calif.) to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR analysis software, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode ANTS may be used in recombinant DNA molecules to direct expression of ANTS, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express ANTS.

As will be understood by those of skill in the art, it may be advantageous to produce ANTS-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter ANTS encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding ANTS may be ligated to a heterologous sequence to encode a fusion protein. For example, to screen peptide libraries for inhibitors of ANTS activity, it may be useful to encode a chimeric ANTS protein that can be recognized by a commercially available antibody. A fusion protein may also be engineered to contain a cleavage site located between the ANTS encoding sequence and the heterologous protein sequence, so that ANTS may be cleaved and purified away from the heterologous moiety.

In another embodiment, sequences encoding ANTS may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of ANTS, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W H Freeman and Co., New York, N.Y.). The composition of the synthetic peptides may be confirmed by amino acid analysis or sequencing (e.g., the Edman degradation procedure; Creighton, supra). Additionally, the amino acid sequence of ANTS, or any part thereof, may be altered during direct synthesis and/or combined using chemical methods with sequences from other proteins, or any part thereof, to produce a variant polypeptide.

In order to express a biologically active ANTS, the nucleotide sequences encoding ANTS or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding ANTS and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding ANTS. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovinis polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding ANTS, vectors based on SV40 or EBV may be used with an appropriate selectable marker.

In bacterial systems, a number of expression vectors may be selected depending upon the use intended for ANTS. For example, when large quantities of ANTS are needed for the induction of antibodies, vectors which direct high level expression of fusion proteins that are readily purified may be used. Such vectors include, but are not limited to, the multifunctional E. coli cloning and expression vectors such as BLUESCRIPT (Stratagene), in which the sequence encoding ANTS may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding ANTS may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express ANTS. For example, in one such system, *Autographa californica* nuclear polyhedrosis virus (AcNPV) is used as a vector to express foreign genes in *Spodoptera frugiperda* cells or in Trichoplusia larvae. The sequences encoding ANTS may be cloned into a non-essential region of the virus, such as the polyhedrin gene, and placed under control of the polyhedrin promoter. Successful insertion of ANTS will render the polyhedrin gene inactive and produce recombinant virus lacking coat protein. The recombinant viruses may then be used to infect, for example, *S. frugiperda* cells or Trichoplusia larvae in which ANTS may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding ANTS may be ligated into an adenovirus transcription/translation complex consisting of the late promoter and tripartite leader sequence. Insertion in a non-essential E1 or E3 region of the viral genome may be used to obtain a viable virus which is capable of expressing ANTS in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding ANTS. Such signals include the ATG initiation codon and adjacent sequences. In cases where sequences encoding ANTS, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express ANTS may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr, which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding ANTS is inserted within a marker gene sequence, transformed cells containing sequences encoding ANTS can be identified by the absence of marker gene function. Alternatively, a marker gene can be placed in tandem with a sequence encoding ANTS under the control of a single promoter. Expression of the marker gene in response to induction or selection usually indicates expression of the tandem gene as well.

Alternatively, host cells which contain the nucleic acid sequence encoding ANTS and express ANTS may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding ANTS can be detected by DNA-DNA or DNA-RNA hybridization or amplification using probes or fragments or fragments of polynucleotides encoding ANTS. Nucleic acid amplification based assays involve the use of oligonucleotides or oligomers based on the sequences encoding ANTS to detect transformants containing DNA or RNA encoding ANTS.

A variety of protocols for detecting and measuring the expression of ANTS, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on ANTS is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding ANTS include oligolabeling, nick translation, end-labeling or PCR amplification using a labeled nucleotide. Alternatively, the sequences encoding ANTS, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp. (Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding ANTS may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode ANTS may be designed to contain signal sequences which direct secretion of ANTS through a prokaryotic or eukaryotic cell membrane. Other constructions may be used to join sequences encoding ANTS to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and ANTS may be used to facilitate purification. One such expression vector provides for expression of a fusion protein containing ANTS and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying ANTS from the fusion protein. A discussion of vectors which contain fusion proteins is provided in Kroll, D. J. et al. (1993; DNA Cell Biol. 12:441–453).

In addition to recombinant production, fragments of ANTS may be produced by direct peptide synthesis using solid-phase techniques (Merrifield, J. (1963) J. Am. Chem. Soc. 85:2149–2154). Protein synthesis may be performed using manual techniques or by automation. Automated synthesis may be achieved, for example, using Applied Biosystems 431A peptide synthesizer (Perkin Elmer). Various fragments of ANTS may be chemically synthesized separately and combined using chemical methods to produce the full length molecule.

THERAPEUTICS

Chemical and structural homology exists between ANTS1 and a human small nuclear ribonucleoprotein, Sm-D (GI 338265; SEQ ID NO:5), and between ANTS2 and a mouse tumor rejection antigen, P35B (GI 199586; SEQ ID NO:6). Northern analysis shows that the expression of ANTS (SEQ ID NO:1 or SEQ ID NO:3) is associated with cancer and fetal/infant development. Therapeutic uses for both polypeptides are described collectively below.

During fetal development, decreased expression of ANTS may cause an increase in apoptosis with no adverse effects to the subject. However, in other situations and in adults, decreased expression of ANTS may cause an increase in apoptosis which is detrimental. Therefore, in one embodiment, ANTS or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, a pharmaceutical composition comprising purified ANTS may be administered to a subject to prevent or treat a disorder associated with increased apoptosis including, but not limited to, those listed above.

In still another embodiment, an agonist which is specific for ANTS may be administered to a subject to prevent or treat a disorder associated with increased apoptosis including, but not limited to, those listed above.

In still another embodiment, a vector capable of expressing ANTS, or a fragment or a derivative thereof, may be administered to a subject to prevent or treat a disorder associated with increased apoptosis including, but not limited to, those listed above.

In a further embodiment, ANTS or a fragment or derivative thereof may be added to cells to stimulate cell proliferation. In particular, ANTS may be added to a cell or cells in vivo using delivery mechanisms such as liposomes, viral based vectors, or electroinjection for the purpose of promoting regeneration or cell differentiation of the cell or cells. In addition, ANTS may be added to a cell, cell line, tissue or organ culture in vitro or ex vivo to stimulate cell proliferation for use in heterologous or autologous transplantation. In some cases, the cell will have been selected for its ability to fight an infection or a cancer or to correct a genetic defect in a disease such as sickle cell anemia, β thalassemia, cystic fibrosis, or Huntington's chorea.

In another further embodiment, an agonist which is specific for ANTS may be administered to a cell to stimulate cell proliferation, as described above.

In another further embodiment, a vector capable of expressing ANTS, or a fragment or a derivative thereof, may be administered to a cell or cells in vivo using delivery mechanisms, or to a cell to stimulate cell proliferation, as described above.

Increased expression of ANTS appears to be associated with increased cell proliferation. Therefore, in one embodiment, an antagonist of ANTS, or a fragment or a derivative thereof, may be administered to a subject to prevent or treat a disorder associated with cell proliferation. Such disorders include various types of cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for ANTS may be used directly as an antagonist, or indirectly as a targeting or delivery mechanism for bringing a pharmaceutical agent to cells or tissue which express ANTS.

In still another embodiment, a vector expressing the complement of the polynucleotide encoding ANTS, or a fragment or a derivative thereof, may be administered to a subject to prevent or treat a disorder associated with cell proliferation including, but not limited to, the types of cancer listed above.

In another embodiment, an antagonist of ANTS, or a fragment or a derivative thereof, may be administered to a subject to prevent or treat inflammation. Disorders associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for ANTS may be used directly as an antagonist, or indirectly as a targeting or delivery mechanism for bringing a pharmaceutical agent to cells or tissue which express ANTS.

In still another embodiment, a vector expressing the complement of the polynucleotide encoding ANTS, or a fragment or a derivative thereof, may be administered to a subject to prevent or treat inflammation associated with any disorder including, but not limited to, those listed above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of ANTS may be produced using methods which are generally known in the art. In particular, purified ANTS may be used to produce antibodies or to screen libraries of pharmaceutical agents to identify those which specifically bind ANTS.

Antibodies to ANTS may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with ANTS or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to ANTS have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of ANTS amino acids may be fused with those of another protein such as keyhole limpet hemocyanin and antibody produced against the chimeric molecule.

Monoclonal antibodies to ANTS may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce ANTS-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for ANTS may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between ANTS and its specific antibody. A two-site, monoclonal-based immunoassay utilizing monoclonal antibodies reactive to two non-interfering ANTS epitopes is preferred, but a competitive binding assay may also be employed (Maddox, supra).

In another embodiment of the invention, the polynucleotides encoding ANTS, or any fragment or complement thereof, may be used for therapeutic purposes. In one aspect, the complement of the polynucleotide encoding ANTS may be used in situations in which it would be desirable to block the transcription of the mRNA. In particular, cells may be transformed with sequences complementary to polynucleotides encoding ANTS. Thus, complementary molecules or fragments may be used to modulate ANTS activity, or to achieve regulation of gene function. Such technology is now well known in the art, and sense or antisense oligonucleotides or larger fragments, can be designed from various locations along the coding or control regions of sequences encoding ANTS.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding ANTS. These techniques are described both in Sambrook et al. (supra) and in Ausubel et al. (supra).

Genes encoding ANTS can be turned off by transforming a cell or tissue with expression vectors which express high levels of a polynucleotide or fragment thereof which encodes ANTS. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding ANTS (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding ANTS.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding ANTS. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of franking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of ANTS, antibodies to ANTS, mimetics, agonists, antagonists, or inhibitors of ANTS. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of ANTS, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example ANTS or fragments thereof, antibodies of ANTS, agonists, antagonists or inhibitors of ANTS, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, which can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind ANTS may be used for the diagnosis of conditions or diseases characterized by expression of ANTS, or in assays to monitor patients being treated with ANTS, agonists, antagonists or inhibitors. The antibodies useful for diagnostic purposes may be prepared in the same manner as those described above for therapeutics. Diagnostic assays for ANTS include methods which utilize the antibody and a label to detect ANTS in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring ANTS are known in the art and provide a basis for diagnosing altered or abnormal levels of ANTS expression. Normal or standard values for ANTS expression are established by combining body fluids or cell extracts taken from normal mammalian subjects, preferably human, with antibody to ANTS under conditions suitable for complex formation. The amount of standard complex formation may be quantified by various methods, but preferably by photometric, means. Quantities of ANTS expressed in subject, control and disease, samples from biopsied tissues are compared with the standard values. Deviation between standard and subject values establishes the parameters for diagnosing disease.

In another embodiment of the invention, the polynucleotides encoding ANTS may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of ANTS may be correlated with disease. The diagnostic assay may be used to distinguish between absence, presence, and excess expression of ANTS, and to monitor regulation of ANTS levels during therapeutic intervention.

In one aspect, hybridization with PCR probes which are capable of detecting polynucleotide sequences, including genomic sequences, encoding ANTS or closely related molecules, may be used to identify nucleic acid sequences which encode ANTS. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding ANTS, alleles, or related sequences.

Probes may also be used for the detection of related sequences, and should preferably contain at least 50% of the nucleotides from any of the ANTS encoding sequences. The hybridization probes of the subject invention may be DNA or RNA and derived from the nucleotide sequence of SEQ ID NO:2, SEQ ID NO:4, or from genomic sequence including promoter, enhancer elements, and introns of the naturally occurring ANTS.

Means for producing specific hybridization probes for DNAs encoding ANTS include the cloning of nucleic acid sequences encoding ANTS or ANTS derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}$P or $^{35}$S, or enzymatic labels, such as alkaline phosphatase coupled to the probe via avidin/biotin coupling systems, and the like.

Polynucleotide sequences encoding ANTS may be used for the diagnosis of conditions or disorders which are associated with expression of ANTS. Examples of such conditions or disorders include, but are not limited to, disorders associated with cell proliferation such as adenocarcinoma, leukemia, lymphoma, melanoma, myeloma, sarcoma, and teratocarcinoma, and particularly, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; disorders with associated inflammation such as Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation,osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma; disorders with associated apoptosis such as AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis. The polynucleotide sequences encoding ANTS may be used in Southern or northern analysis, dot blot, or other membrane-based technologies; in PCR technologies; or in dipstick, pin, ELISA assays or microarrays utilizing fluids or tissues from patient biopsies to detect altered ANTS expression. Such qualitative or quantitative methods are well known in the art.

In a particular aspect, the nucleotide sequences encoding ANTS may be useful in assays that detect activation or induction of various cancers, particularly those mentioned above. The nucleotide sequences encoding ANTS may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding ANTS in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of ANTS, a normal or standard profile for expression is established. This may be accomplished by combining body fluids or cell extracts taken from normal subjects, either animal or human, with a sequence, or a fragment thereof, which encodes ANTS, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding ANTS may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of ANTS include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode ANTS may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding ANTS on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, ANTS, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between ANTS and the agent being tested, may be measured.

Another technique for drug screening which may be used provides for high throughput screening of compounds having suitable binding affinity to the protein of interest as described in published PCT application WO84/03564. In this method, as applied to ANTS large numbers of different small test compounds are synthesized on a solid substrate, such as plastic pins or some other surface. The test compounds are reacted with ANTS, or fragments thereof, and washed. Bound ANTS is then detected by methods well known in the art. Purified ANTS can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding ANTS specifically compete with a test compound for binding ANTS. In this manner, the antibodies can be used to detect the presence of any peptide which shares one or more antigenic determinants with ANTS.

In additional embodiments, the nucleotide sequences which encode ANTS may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

The LUNGNOT01 cDNA library was constructed using polyA RNA using RNA isolated from the lung tissue of a 72-year-old male. The tissue was lysed in a buffer containing GuSCN, and the lysate was centrifuged over a 5.7M CsCl cushion using an Beckman SW28 rotor in a Beckman L8-70M Ultracentrifuge (Beckman Instruments) for 18 hours at 25,000 rpm at ambient temperature. The RNA was extracted with phenol chloroform pH 8.0, precipitated using 0.3M sodium acetate and 2.5 volumes of ethanol, resuspended in water and DNase treated for 15 min at 37° C. The RNA was isolated using the OLIGOTEX kit (QIAGEN, Chatsworth, Calif.) and used to construct the cDNA library.

First strand cDNA synthesis was accomplished using an oligo d(T) primer/linker which also contained an XhoI restriction site. Second strand synthesis was performed using a combination of DNA polymerase I, E. coli ligase and RNase H, followed by the addition of an EcoRI adaptor to the blunt ended cDNA. The EcoRI adapted, double-stranded cDNA was then digested with XhoI restriction enzyme and fractionated on Sephacryl S400 to obtain sequences which exceeded 1000 bp in size. The size selected cDNAs were inserted into the UNIZAP vector system (Stratagene); and the vector, which contains the PBLUESCRIPT phagemid (Stratagene), was transformed into cells of E. coli, strain XL1-BLUEMRF (Stratagene).

The BLADNOT04 cDNA library was constructed using polyA RNA isolated from bladder tissue of a 28-year-old Caucasian male, who died from a self-inflicted gunshot wound. The frozen tissue was homogenized and lysed using a Polytron PT-3000 homogenizer (Brinkmann Instruments, Westbury, N.Y.) in guanidinium isothiocyanate solution. The lysates were centrifuged over a 5.7M CsCl cushion using a Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3M sodium acetate and 2.5 volumes of ethanol, resuspended in RNAse-free water, and DNase treated at 37° C. RNA extraction and precipitation were repeated as before. The mRNA was then isolated using the OLIGOTEX kit (QIAGEN) and used to construct the cDNA libraries.

The mRNA was handled according to the recommended protocols in the SUPERSCRIPT plasmid system for cDNA synthesis and plasmid cloning (Cat. #18248-013, Gibco/BRL). cDNAs were fractionated on a SEPHAROSE CL4B column (Cat. #275105-01, Pharmacia), and those cDNAs exceeding 400 bp were ligated into pINCY 1 (Incyte Pharmaceuticals, Palo Alto Calf.). The plasmid pINCY 1 (Incyte Pharmaceuticals) was subsequently transformed into DH5α competent cells (Cat. #18258-012, Gibco/BRL).

II Isolation and Sequencing of cDNA Clones

The phagemid forms of individual cDNA clones were obtained by the in vivo excision process. Enzymes from both PBLUESCRIPT plasmid and a cotransformed f1 helper phage nicked the DNA, initiated new DNA synthesis, and created the smaller, single-stranded circular phagemid DNA molecules which contained the cDNA insert. The phagemid DNA was released, purified, and used to reinfect fresh SOLR host cells (Stratagene). Presence of the phagemid which carries the gene for β-lactamase allowed transformed bacteria to grow on medium containing ampicillin.

Plasmid DNA was released from the cells and purified using the R.E.A.L. Prep 96 plasmid kit (Catalog #26173, QIAGEN). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, GIBCO/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a MICROLAB 2200 (Hamilton, Reno, Nev.) in combination with Peltier thermalcyclers (PTC200 from MJ Research, Watertown, Mass.) and Applied Biosystems 377 DNA sequencing systems and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul S F (1993) J. Mol. Evol. 36:290–300; Altschul, S F et al. (1990) J. Mol. Biol. 215:403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R F and T F Smith (1992 Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin and Altschul (1993; Proc Nat Acad Sci 90:5873–7) and incorporated herein by reference, searches matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) *J.Mol.Evol.* 36:290–300; Altschul, S. F. et al. (1990) *J.Mol.Evol.* 215:403–410) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\%\ \text{sequence identity} \times \%\ \text{maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding ANTS occurs. Abundance and percent abundance are also reported. Abundance directly reflects the number of times a particular transcript is represented in a cDNA library, and percent abundance is abundance divided by the total number of sequences examined in the cDNA library.

V Extension of ANTS Encoding Polynucleotides

The nucleic acid sequence of the Incyte Clone 124208 or 1318190 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 primer analysis software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer—primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier thermal cycler (PTC200; M.J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat steps 4–6 for 15 additional cycles
Step 8 94° C. for 15 sec
Step 9 65° C. for 1 min
Step 10 68° C. for 7:15 min
Step 11 Repeat steps 8–10 for 12 cycles
Step 12 72° C. for 8 min
Step 13 4° C. (and holding)

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK silica-gel purification system (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent *E. coli* cells (in 40 µl of appropriate media) were transformed with 3 µl of ligation mixture and cultured in 80 µl of SOC medium (Sambrook et al., supra). After incubation for one hour at 37° C., the *E. coli* mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 or SEQ ID NO:4, is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 or SEQ ID NO:4 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 primer analysis software (National Biosciences), labeled by combining 50 pmol of each oligomer and 250 μCi of [γ-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1 × saline sodium citrate and 0.5% sodium dodecyl sulfate. After XOMAT AR film (Kodak, Rochester, N.Y.) is exposed to the blots, or the blots are exposed to a Phosphoimager cassette (Molecular Dynamics, Sunnyvale, Calif.), hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the microarray.

VIII Complementary Polynucleotides

Sequence complementary to the ANTS-encoding sequence, or any part thereof, is used to decrease or inhibit expression of naturally occurring ANTS. Although use of oligonucleotides comprising from about 15 to about 30 base-pairs is described, essentially the same procedure is used with smaller or larger sequence fragments. Appropriate oligonucleotides are designed using OLIGO 4.06 software and the coding sequence of ANTS, SEQ ID NO:1 or SEQ ID NO:3. To inhibit transcription, a complementary oligonucleotide is designed from the most unique 5' sequence and used to prevent promoter binding to the coding sequence. To inhibit translation, a complementary oligonucleotide is designed to prevent ribosomal binding to the ANTS-encoding transcript.

IX Expression of ANTS

Expression of ANTS is accomplished by subcloning the cDNAs into appropriate vectors and transforming the vectors into host cells. In this case, the cloning vector is also used to express ANTS in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of ANTS into the bacterial growth media which can be used directly in the following assay for activity.

X Demonstration of ANTS Activity

ANTS can be expressed by transforming a mammalian cell line such as COS7, HeLa or CHO with an eukaryotic expression vector encoding ANTS. Eukaryotic expression vectors are commercially available, and the techniques to introduce them into cells are well known to those skilled in the art. The cells are incubated for 48–72 hours after transformation under conditions appropriate for the cell line to allow expression of ANTS. Then, phase microscopy is used to compare the mitotic index of transformed versus control cells. An increase in the mitotic index indicates ANTS activity.

XI Production of ANTS Specific Antibodies

ANTS that is substantially purified using PAGE electrophoresis (Sambrook, supra), or other purification techniques, is used to immunize rabbits and to produce antibodies using standard protocols. The anmino acid sequence deduced from SEQ ID NO:2 or SEQ ID NO:4 is analyzed using DNASTAR software (DNASTAR Inc.) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Model 431A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring ANTS Using Specific Antibodies

Naturally occurring or recombinant ANTS is substantially purified by immunoaffinity chromatography using antibodies specific for ANTS. An immunoaffinity column is constructed by covalently coupling ANTS antibody to an activated chromatographic resin, such as CNBr-activated SEPHAROSE (Pharmacia & Upjohn). After the coupling, the resin is blocked and washed according to the manufacturer's instructions.

Media containing ANTS is passed over the immunoaffinity column, and the column is washed under conditions that allow the preferential absorbance of ANTS (e.g., high ionic strength buffers in the presence of detergent). The column is eluted under conditions that disrupt antibody/ANTS binding (eg, a buffer of pH 2–3 or a high concentration of a chaotrope, such as urea or thiocyanate ion), and ANTS is collected.

XIII Identification of Molecules Which Interact with ANTS

ANTS or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled ANTS, washed and any wells with labeled ANTS complex are assayed. Data obtained using different concentrations of ANTS are used to calculate values for the number, affinity, and association of ANTS with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 123 amino acids
      (B) TYPE: amino acid
      (C) STRANDEDNESS: single
      (D) TOPOLOGY: linear (vii) IMMEDIATE SOURCE:
      (A) LIBRARY: LUNGNOT01
      (B) CLONE: 124208

(xi) SEQUENCE DESCRIPTION: SEQ ID NO:1:

Met Ala Val Ser His Ser Val Lys Glu Arg Thr Ile Ser Glu Asn Ser
 1          5              10             15

```
Leu Ile Ile Leu Leu Gln Gly Leu Gln Gly Arg Val Thr Thr Val Asp
             20                  25                  30

Leu Arg Asp Glu Ser Val Ala His Gly Arg Ile Asp Asn Val Asp Ala
         35                  40                  45

Phe Met Asn Ile Arg Leu Ala Lys Val Thr Tyr Thr Asp Arg Trp Gly
 50                  55                  60

His Gln Val Lys Leu Asp Asp Leu Phe Val Thr Gly Arg Asn Val Arg
 65                  70                  75                  80

Tyr Val His Ile Pro Asp Asp Val Asn Ile Thr Ser Thr Ile Glu Gln
                 85                  90                  95

Gln Leu Gln Ile Ile His Arg Val Arg Asn Phe Gly Gly Lys Gly Gln
             100                 105                 110

Gly Arg Trp Glu Phe Pro Pro Lys Asn Cys Lys
         115                 120
```

(2) INFORMATION FOR SEQ ID NO:2:

(i) SEQUENCE CHARACTERISTICS:
        (A) LENGTH: 876 base pairs
        (B) TYPE: nucleic acid
        (C) STRANDEDNESS: single
        (D) TOPOLOGY: linear (vii) IMMEDIATE SOURCE:
        (A) LIBRARY: LUNGNOT01
        (B) CLONE: 124208

(xi) SEQUENCE DESCRIPTION: SEQ ID NO:2:

```
CGCACTCTGC GCCCGGAGGA CAGAGCGGCC CGGTCGCCGG CATGGTTTCT CCGTCCTGCT    60

GCAGCCGGCG GGAGGCAGCC AGTCCAGGCG CCCGCTAGCT TCGGCGGCGA CCCAGACGGG   120

GAAAGCGGAA GGAATGTCGC GTGCAAGCAG GCAGCTGGTG TGGAAGAATG GCGGTGAGCC   180

ATTCAGTGAA GGAGCGGACC ATCTCTGAGA ACAGCCTGAT CATCCTACTG CAGGGCCTCC   240

AGGGCCGGGT AACCACTGTG GACCTGCGGG ATGAGAGCGT GGCCCACGGA CGCATAGACA   300

ATGTCGATGC TTTCATGAAC ATCCGCCTGG CCAAAGTCAC CTACACGGAC CGTTGGGGGC   360

ATCAGGTCAA GCTGGATGAC CTCTTTGTGA CAGGCCGCAA TGTCCGCTAC GTCCACATCC   420

CAGATGACGT GAACATCACC TCGACCATTG AGCAGCAGCT GCAGATTATC CATCGGGTGC   480

GAAACTTTGG TGGCAAGGGC CAAGGCCGGT GGGAATTTCC CCCAAAAAAC TGTAAGTGAG   540

GCCCTCAGCA AGCCCTGGCC CCAACTCGGA GTCCTCCAGT GATCTCCGGA GCTAGTTCCC   600

TGCCCTCACA CCCTGTCTGG TACCCGAGAA GAAAGCAGGG CCAGGCCAGA AGCTGGTGTC   660

CAACAGACAC CACCTGTCAA AGCTGCCTTT CACAGGGTTC CACCTCCCAG ACTCACTCTG   720

GGACCCAGAA TCCTATATGT GGCCTTGGGG TAGGTGACAA TCCCCCTTTT TGATGATCTG   780

AATCTCTGAC TTATTGATTA TGGAACCTGT CAAGTAGTTT TCAACTCTCC CAGTGAGGAT   840

AATTAAACAT GCTCAGCCTG AAAAAAAAAA AAAAAA                             876
```

(2) INFORMATION FOR SEQ ID NO:3:

(i) SEQUENCE CHARACTERISTICS:
        (A) LENGTH: 321 amino acids
        (B) TYPE: amino acid
        (C) STRANDEDNESS: single
        (D) TOPOLOGY: linear (vii) IMMEDIATE SOURCE:
        (A) LIBRARY: BLADNOT04
        (B) CLONE: 1318190

(xi) SEQUENCE DESCRIPTION: SEQ ID NO:3:

| Met | Gly | Glu | Pro | Gln | Gly | Ser | Met | Arg | Ile | Leu | Val | Thr | Gly | Gly | Ser |
|---|---|---|---|---|---|---|---|---|---|---|---|---|---|---|---|
| 1 | | | | 5 | | | | | 10 | | | | | 15 | |

| Gly | Leu | Val | Gly | Lys | Ala | Ile | Gln | Lys | Val | Val | Ala | Asp | Gly | Ala | Gly |
|---|---|---|---|---|---|---|---|---|---|---|---|---|---|---|---|
| | | | 20 | | | | | 25 | | | | | 30 | | |

| Leu | Pro | Gly | Glu | Asp | Trp | Val | Phe | Val | Ser | Ser | Lys | Asp | Ala | Asp | Leu |
|---|---|---|---|---|---|---|---|---|---|---|---|---|---|---|---|
| | | | 35 | | | | | 40 | | | | | 45 | | |

| Thr | Asp | Thr | Ala | Gln | Thr | Arg | Ala | Leu | Phe | Glu | Lys | Val | Gln | Pro | Thr |
|---|---|---|---|---|---|---|---|---|---|---|---|---|---|---|---|
| | 50 | | | | | 55 | | | | | 60 | | | | |

| His | Val | Ile | His | Leu | Ala | Ala | Met | Val | Gly | Gly | Leu | Phe | Arg | Asn | Ile |
|---|---|---|---|---|---|---|---|---|---|---|---|---|---|---|---|
| 65 | | | | | 70 | | | | | 75 | | | | | 80 |

| Lys | Tyr | Asn | Leu | Asp | Phe | Trp | Arg | Lys | Asn | Val | His | Met | Asn | Asp | Asn |
|---|---|---|---|---|---|---|---|---|---|---|---|---|---|---|---|
| | | | | 85 | | | | | 90 | | | | | 95 | |

| Val | Leu | His | Ser | Ala | Phe | Glu | Val | Gly | Ala | Arg | Lys | Val | Val | Ser | Cys |
|---|---|---|---|---|---|---|---|---|---|---|---|---|---|---|---|
| | | | 100 | | | | | 105 | | | | | 110 | | |

| Leu | Ser | Thr | Cys | Ile | Phe | Pro | Asp | Lys | Thr | Thr | Tyr | Pro | Ile | Asp | Glu |
|---|---|---|---|---|---|---|---|---|---|---|---|---|---|---|---|
| | | | 115 | | | | | 120 | | | | | 125 | | |

| Thr | Met | Ile | His | Asn | Gly | Pro | Pro | His | Asn | Ser | Asn | Phe | Gly | Tyr | Ser |
|---|---|---|---|---|---|---|---|---|---|---|---|---|---|---|---|
| | 130 | | | | | 135 | | | | | 140 | | | | |

| Tyr | Ala | Lys | Arg | Met | Ile | Asp | Val | Gln | Asn | Arg | Ala | Tyr | Phe | Gln | Gln |
|---|---|---|---|---|---|---|---|---|---|---|---|---|---|---|---|
| 145 | | | | | 150 | | | | | 155 | | | | | 160 |

| Tyr | Gly | Cys | Thr | Phe | Thr | Ala | Val | Ile | Pro | Thr | Asn | Val | Phe | Gly | Pro |
|---|---|---|---|---|---|---|---|---|---|---|---|---|---|---|---|
| | | | | 165 | | | | | 170 | | | | | 175 | |

| His | Asp | Asn | Phe | Asn | Ile | Glu | Asp | Gly | His | Val | Leu | Pro | Gly | Leu | Ile |
|---|---|---|---|---|---|---|---|---|---|---|---|---|---|---|---|
| | | | 180 | | | | | 185 | | | | | 190 | | |

| His | Lys | Val | His | Leu | Ala | Lys | Ser | Ser | Gly | Ser | Ala | Leu | Thr | Val | Trp |
|---|---|---|---|---|---|---|---|---|---|---|---|---|---|---|---|
| | | 195 | | | | | 200 | | | | | 205 | | | |

| Gly | Thr | Gly | Asn | Pro | Arg | Arg | Gln | Phe | Ile | Tyr | Ser | Leu | Asp | Leu | Ala |
|---|---|---|---|---|---|---|---|---|---|---|---|---|---|---|---|
| | 210 | | | | | 215 | | | | | 220 | | | | |

| Gln | Leu | Phe | Ile | Trp | Val | Leu | Arg | Glu | Tyr | Asn | Glu | Val | Glu | Pro | Ile |
|---|---|---|---|---|---|---|---|---|---|---|---|---|---|---|---|
| 225 | | | | | 230 | | | | | 235 | | | | | 240 |

| Ile | Leu | Ser | Val | Gly | Glu | Asp | Gly | Val | Ser | Ile | Lys | Glu | Ala | Ala |
|---|---|---|---|---|---|---|---|---|---|---|---|---|---|---|
| | | | | 245 | | | | | 250 | | | | | 255 |

| Glu | Ala | Val | Val | Glu | Ala | Met | Asp | Phe | His | Gly | Val | Thr | Phe | Asp |
|---|---|---|---|---|---|---|---|---|---|---|---|---|---|---|
| | | | 260 | | | | | 265 | | | | | 270 | |

| Thr | Thr | Lys | Ser | Asp | Gly | Gln | Phe | Lys | Lys | Thr | Ala | Ser | Asn | Ser | Lys |
|---|---|---|---|---|---|---|---|---|---|---|---|---|---|---|---|
| | | 275 | | | | | 280 | | | | | 285 | | | |

| Leu | Arg | Thr | Tyr | Leu | Pro | Asp | Phe | Arg | Phe | Thr | Pro | Phe | Lys | Gln | Ala |
|---|---|---|---|---|---|---|---|---|---|---|---|---|---|---|---|
| | 290 | | | | | 295 | | | | | 300 | | | | |

| Val | Lys | Glu | Thr | Cys | Ala | Trp | Phe | Thr | Asp | Asn | Tyr | Glu | Gln | Ala | Arg |
|---|---|---|---|---|---|---|---|---|---|---|---|---|---|---|---|
| 305 | | | | | 310 | | | | | 315 | | | | | 320 |

Lys (2) INFORMATION FOR SEQ ID NO:4:

(i) SEQUENCE CHARACTERISTICS:
        (A) LENGTH: 1352 base pairs
        (B) TYPE: nucleic acid
        (C) STRANDEDNESS: single
        (D) TOPOLOGY: linear (vii) IMMEDIATE SOURCE:
        (A) LIBRARY: BLADNOT04
        (B) CLONE: 1318190

(xi) SEQUENCE DESCRIPTION: SEQ ID NO:4:

TGGNAGCCGG CGGTGGGGCT GGACGCAGTG AGGTGGCACC GGACTCAGCC GCGCCCTGGG    60

```
CCCTGGATGT TCCGTGCAAC TGACATGGGT GAACCCCAGG GATCCATGCG GATTCTAGTG      120

ACAGGGGGCT CTGGGCTGGT AGGCAAAGCC ATCCAGAAGG TGGTAGCAGA TGGAGCTGGA      180

CTTCCTGGAG AGGACTGGGT GTTTGTCTCC TCTAAAGACG CCGATCTCAC GGATACAGCA      240

CAGACCCGCG CCCTGTTTGA GAAGGTCCAA CCCACACACG TCATCCATCT TGCTGCAATG      300

GTGGGGGGCC TGTTCCGGAA TATCAAATAC AATTTGGACT TCTGGAGGAA AAACGTGCAC      360

ATGAACGACA ACGTCCTGCA CTCGGCCTTT GAGGTGGGCG CCCGCAAGGT GGTGTCCTGC      420

CTGTCCACCT GTATCTTCCC TGACAAGACG ACCTACCCGA TAGATGAGAC CATGATCCAC      480

AATGGGCCTC CCCACAACAG CAATTTTGGG TACTCGTATG CCAAGAGGAT GATCGACGTG      540

CAGAACAGGG CCTACTTCCA GCAGTACGGC TGCACCTTCA CCGCTGTCAT CCCCACCAAC      600

GTCTTCGGGC CCCACGACAA CTTCAACATC GAGGATGGCC ACGTGCTGCC TGGCCTCATC      660

CACAAGGTGC ACCTGGCCAA GAGCAGCGGC TCGGCCCTGA CGGTGTGGGG TACAGGGAAT      720

CCGCGGAGGC AGTTCATATA CTCGCTGGAC CTGGCCCAGC TCTTTATCTG GGTCCTGCGG      780

GAGTACAATG AAGTGGAGCC CATCATCCTC TCCGTGGGCG AGGAAGATGA GGTCTCCATC      840

AAGGAGGCAG CCGAGGCGGT GGTGGAGGCC ATGGACTTCC ATGGGAAGT CACCTTTGAT      900

ACAACCAAGT CGGATGGGCA GTTTAAGAAG ACAGCCAGTA ACAGCAAGCT GAGGACCTAC      960

CTGCCCGACT TCCGGTTCAC ACCCTTCAAG CAGGCGGTGA AGGAGACCTG TGCTTGGTTC     1020

ACTGACAACT ACGAGCAGGC CCGGAAGTGA AGCTGAAGA CAGGATCAGG TGCCAGCGGA     1080

CCATCGGCTG GCAGAGCCCA GCGGCCACCA CCCGTCAACC CTGCCAGGAG CTGAGGGCAC     1140

CACCCAGCAA CCTGGGCCTG CATTCCATCC GCTCTGCAGC CCAAGCATC TTTCCAGTGG     1200

GGCCCCCATT CACGTTGGTC CTCAGGGAAA CCAGGGTCCG GGGCAGGCCC GGCGCTTTGC     1260

TCCCCACACC AGCCCCCTGC GCGTGTCCAC TCTGATCCTG CATCCCACTC CCTGGGAGCC     1320

AATAAAGTGC ATTTTCACAG GCAAAAAAAA AA                                   1352
```

(2) INFORMATION FOR SEQ ID NO:5:

(i) SEQUENCE CHARACTERISTICS:
        (A) LENGTH: 119 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 338265

(xi) SEQUENCE DESCRIPTION: SEQ ID NO:5:

```
Met Lys Leu Val Arg Phe Leu Met Lys Leu Ser His Glu Thr Val Thr
 1               5                  10                  15

Ile Glu Leu Lys Asn Gly Thr Gln Val His Gly Thr Ile Thr Gly Val
                20                  25                  30

Asp Val Ser Met Asn Thr His Leu Lys Ala Val Lys Met Thr Leu Lys
            35                  40                  45

Asn Arg Glu Pro Val Gln Leu Glu Thr Leu Ser Ile Arg Gly Asn Asn
    50                  55                  60

Ile Arg Tyr Phe Ile Leu Pro Asp Ser Leu Pro Leu Asp Thr Leu Leu
65                  70                  75                  80

Val Asp Val Glu Pro Lys Val Lys Ser Lys Lys Arg Glu Ala Val Ala
                85                  90                  95

Gly Arg Gly Arg Gly Arg Gly Arg Gly Arg Gly Arg Gly Arg Gly Arg
               100                 105                 110
```

```
Gly Arg Gly Gly Pro Arg Arg
            115

(2) INFORMATION FOR SEQ ID NO:6:

(i) SEQUENCE CHARACTERISTICS:
        (A) LENGTH: 271 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 199586

(xi) SEQUENCE DESCRIPTION: SEQ ID NO:6:

Met Gly Glu Pro His Gly Ser Met Arg Ile Leu Val Thr Gly Gly Ser
1               5                   10                  15

Gly Leu Val Gly Arg Ala Ile Gln Lys Val Ala Asp Gly Ala Gly
            20                  25                  30

Leu Pro Gly Glu Glu Trp Val Phe Val Ser Ser Lys Asp Ala Asp Leu
            35                  40                  45

Thr Asp Ala Ala Gln Thr Gln Ala Leu Phe Gln Lys Val Gln Pro Thr
    50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Val His Ile Asn Asp Asn
                85                  90                  95

Val Leu His Ser Ala Phe Glu Val Gly Ala Arg Lys Val Val Ser Cys
            100                 105                 110

Leu Ser Thr Cys Ile Phe Pro Asp Lys Thr Thr Tyr Pro Ile Asp Glu
            115                 120                 125

Thr Met Ile His Asn Gly Pro Pro His Ser Ser Asn Phe Gly Tyr Ser
    130                 135                 140

Tyr Ala Lys Arg Met Ile Asp Val Gln Asn Arg Ala Tyr Phe Gln Gln
145                 150                 155                 160

His Phe Cys Thr Phe Thr Ala Val Ile Pro Thr Asn Val Phe Gly Pro
                165                 170                 175

Tyr Asp Asn Phe Asn Ile Glu Asp Gly His Val Leu Pro Gly Leu Ile
                180                 185                 190

His Lys Val His Leu Ala Lys Ser Ser Asp Ser Ala Leu Thr Val Trp
            195                 200                 205

Gly Thr Gly Lys Pro Arg Arg Gln Phe Ile Tyr Ser Leu Asp Leu Ala
    210                 215                 220

Arg Leu Phe Ile Trp Val Leu Arg Glu Tyr Ser Glu Val Glu Pro Ile
225                 230                 235                 240

Ile Leu Ser Val Gly Glu Glu Asp Glu Val Ser Ile Lys Glu Ala Ala
            245                 250                 255

Glu Ala Val Val Glu Ala Met Asp Phe Asn Gly Gly Ser His Phe
            260                 265                 270
```

What is claimed is:

1. An isolated and purified polynucleotide encoding a polypeptide comprising the amino acid sequence of SEQ ID NO:1.

2. A composition comprising the polynucleotide of claim 1 and an acceptable carrier.

3. An isolated and purified polynucleotide which hybridizes under stringent wash conditions of 0.1× saline sodium citrate and 0.5% sodium dodecyl sulfate to the polynucleotide of claim 1.

4. An isolated and purified polynucleotide which is completely complementary to the polynucleotide of claim 1.

5. An isolated and purified polynucleotide comprising SEQ ID NO:2.

6. A composition comprising the polynucleotide of claim 5 and an acceptable carrier.

7. An isolated and purified polynucleotide which is completely complementary to the polynucleotide of claim 5.

8. An expression vector containing the polynucleotide of claim 1.

9. A host cell containing the expression vector of claim 8.

10. A method for producing a polypeptide comprising the amino acid sequence of SEQ ID NO:1, the method comprising the steps of:
   a) culturing the host cell of claim 9 under conditions suitable for the expression of the polypeptide; and
   b) recovering the polypeptide from the host cell culture.

11. A method for detecting a polynucleotide encoding a polypeptide comprising the amino acid sequence of SEQ ID NO:1 in a biological sample containing nucleic acid material, the method comprising the steps of:

a) hybridizing the polynucleotide of claim 6 to the nucleic acid material of the biological sample, thereby forming a hybridization complex; and b) detecting the hybridization complex, wherein the presence of the complex correlates with the presence of the polynucleotide encoding the polypeptide comprising the amino acid sequence of SEO ID NO:1 in the biological sample.

12. The method of claim 11 wherein the nucleic acid material is amplified by the polymerase chain reaction prior to the hybridizing step.

* * * * *